(12) United States Patent
Sorbo et al.

(10) Patent No.: US 10,568,864 B2
(45) Date of Patent: *Feb. 25, 2020

(54) LIQUID CARBON DIOXIDE BOTANICAL EXTRACTION SYSTEM

(71) Applicant: Cool Clean Technologies, LLC, Eagan, MN (US)

(72) Inventors: Nelson W. Sorbo, Temecula, CA (US); Jon R. Turner, Minneapolis, MN (US); Jon Wikstrom, Eagan, MN (US)

(73) Assignee: Cool Clean Technologies, LLC, Eagan, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/283,140

(22) Filed: Feb. 22, 2019

(65) Prior Publication Data

US 2019/0183848 A1  Jun. 20, 2019

Related U.S. Application Data

(63) Continuation of application No. 15/633,079, filed on Jun. 26, 2017, now Pat. No. 10,265,295.

(60) Provisional application No. 62/354,354, filed on Jun. 24, 2016.

(51) Int. Cl.
| | | |
|---|---|---|
| *A61K 36/00* | (2006.01) | |
| *A61K 31/352* | (2006.01) | |
| *A61K 31/465* | (2006.01) | |
| *A61K 36/185* | (2006.01) | |
| *A61K 36/81* | (2006.01) | |

(52) U.S. Cl.
CPC .......... *A61K 31/352* (2013.01); *A61K 31/465* (2013.01); *A61K 36/185* (2013.01); *A61K 36/81* (2013.01); *A61K 2236/00* (2013.01)

(58) Field of Classification Search
CPC .................................................... A61K 36/00
USPC ....................................................... 424/725
See application file for complete search history.

(56) References Cited

U.S. PATENT DOCUMENTS

| | | |
|---|---|---|
| 5,490,884 A | 2/1996 | Robinson et al. |
| 6,106,720 A | 8/2000 | Kanel et al. |
| 6,403,126 B1 | 6/2002 | Webster et al. |
| 7,344,736 B2 | 3/2008 | Whittle et al. |
| 7,622,140 B2 | 11/2009 | Whittle et al. |
| 8,501,250 B2 | 8/2013 | Ismail et al. |
| 9,044,390 B1 | 6/2015 | Speier |
| 9,186,386 B2 | 11/2015 | Speier |
| 9,296,979 B1 | 3/2016 | Kuo et al. |
| 2004/0147767 A1 | 7/2004 | Whittle et al. |
| 2008/0103193 A1 | 5/2008 | Castor et al. |
| 2010/0119606 A1 | 3/2010 | Whittle et al. |
| 2013/0253210 A1 | 9/2013 | Ismail et al. |
| 2014/0248379 A1 | 9/2014 | Mueller |

FOREIGN PATENT DOCUMENTS

| | | |
|---|---|---|
| CA | 2424356 A1 | 4/2003 |
| EP | 2275097 A1 | 1/2011 |
| RU | 2060263 C1 | 5/1996 |
| RU | 2582978 C2 | 7/2015 |
| WO | WO2000009647 A1 | 2/2000 |

OTHER PUBLICATIONS

International Search Report of corresponding PCT application PCT/US 2017/039122 dated Sep. 21, 2017.
Pertinent patent prosecution history of parent U.S. Appl. No. 15/633,079.

*Primary Examiner* — Michael V Meller
(74) *Attorney, Agent, or Firm* — DuFault Law Firm, P.C.; Dustin R. DuFault

(57) ABSTRACT

A process is disclosed for extracting cannabinoids from plant materials. The process comprises providing a pressurizable extraction vessel having a rotatable drum with baffles, along with providing a solvent permeable filter bag. The plant material is placed within the filter bag, and the filter bag containing the plant material is placed within the extraction vessel. The extraction vessel is then filled with subcritical liquid carbon dioxide and rotated to so that the plant material is in contact with the liquid carbon dioxide. After a selected period of time, the liquid carbon dioxide solvent containing the cannabinoid extracted from the plant material is removed from the vessel, and sent to a separator. The separator separates the cannabinoid from the liquid carbon dioxide solvent.

6 Claims, 9 Drawing Sheets

FIG. 5
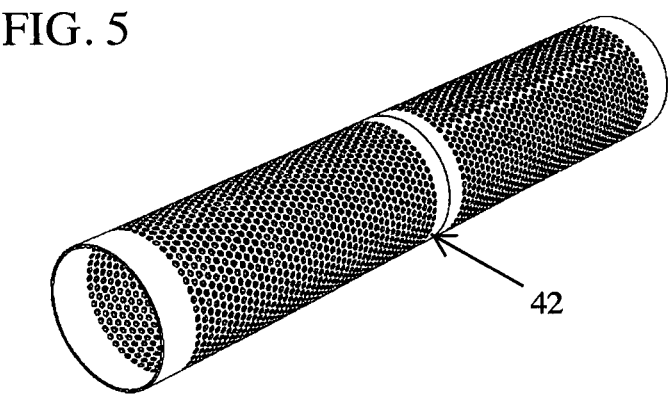
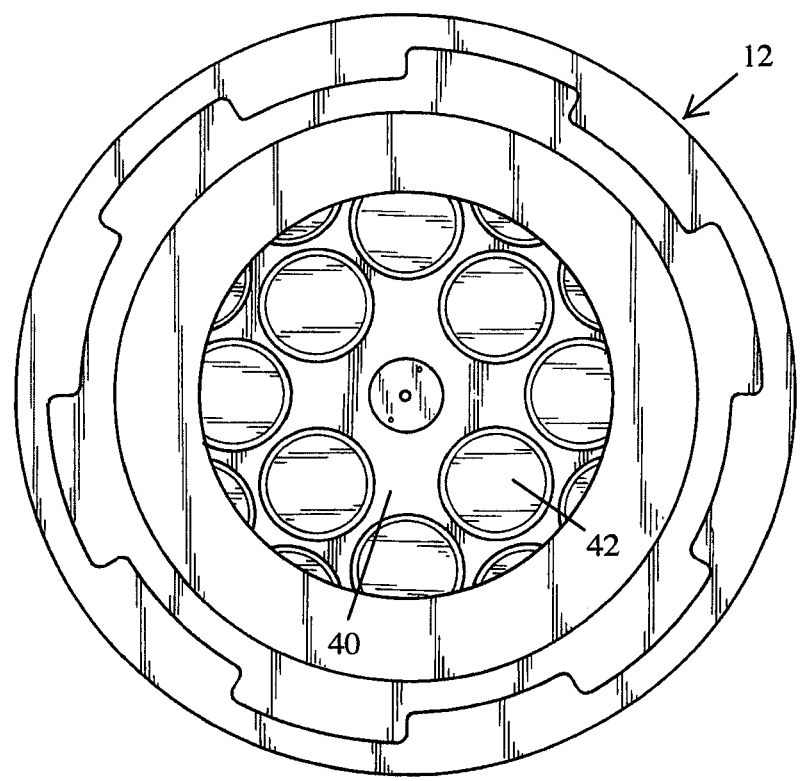
FIG. 6

LIQUID CARBON DIOXIDE BOTANICAL EXTRACTION SYSTEM

CROSS-REFERENCE TO RELATED APPLICATION(S)

The present application claims a benefit of similarly entitled U.S. Nonprovisional application Ser. No. 15/633,079, filed Jun. 26, 2017, which claimed the benefit of similarly entitled U.S. Provisional Application No. 62/354,354, filed Jun. 24, 2016, the contents of which are incorporated herein in their entireties by this reference.

BACKGROUND OF THE INVENTION

The present invention generally relates to a carbon dioxide based extraction system. More particularly, the present invention relates to an extraction system utilizing subcritical liquid carbon dioxide to extract compounds from botanical materials.

Botanical materials contain a variety of extractable compounds that are useful for many applications. For example, certain cannabinoids obtained from industrial hemp can be used for medicinal purposes, including the treatment of cramps, migraines, nausea, asthma and convulsions.

Carbon dioxide has been demonstrated in the past to be useful in extracting compounds from botanical materials. For example, there is known in the art supercritical carbon dioxide extraction systems, having pressures greater than 7.4 MPa and temperatures greater than 31° C., to be commonly used to extract compounds from botanical materials. There are also known in the art subcritical carbon dioxide extraction systems, having pressures and temperatures below the critical point of carbon dioxide. While these systems can be effective, they are expensive in both capital and operating costs, especially for supercritical systems, and frequently require either substantial pre-treatment or post-extraction treatments to produce an extract with the desired quality.

Therefore, there exists a need to provide a cleaning system which can effectively and efficiently extract organic compounds from botanical materials and minimize post-extraction treatments.

BRIEF SUMMARY OF INVENTION

The present invention includes a process for extracting cannabinoids from plant material. The process comprises first providing a pressurizable extraction vessel. The extraction vessel may have a rotatable drum positioned in a horizontal fashion having either baffles, or plurality of perforated containers. Alternatively, the extraction vessel may have a drum positioned in a vertical fashion wherein circulation of solvent is permitted through the drum via an impeller. The process of the present invention further includes providing one or more solvent permeable filter bags, having pores of 0.5 microns or greater, for containing plant or botanical material during the extraction process. Upon filling the one or more filter bags with the plant or botanical material to be treated, each filter bag is positioned within the extraction vessel, either within the drum with baffles, or within the perforated container or containers positioned within the drum. Upon sealing the extraction vessel, the extraction vessel is filled subcritical liquid carbon dioxide, preferably at a pressure between 2.76 to 4.99 MPa and a temperature between −10 to 14° C. The drum is then either rotated, or the impeller activated, depending upon the embodiment, each to effect agitation of the subcritical liquid carbon dioxide with the plant or botanical material. The subcritical liquid carbon dioxide is then allowed to be in contact with the plant or botanical material for a selected amount of time to extract at least a portion of the cannabinoids from the plant material into the subcritical liquid carbon dioxide solvent. Afterwards, the subcritical liquid carbon dioxide now containing the cannabinoid extracted from the plant or botanical material is removed from the extraction vessel, and distilled to result a purified extractant. The extraction vessel is depressurized, and the filter bags containing the plant material are removed therefrom for disposal or further desired processing.

BRIEF DESCRIPTION OF THE DRAWINGS

The following figures are used herein in conjunction with the written description to assist in understanding the invention. The Figures are as follows:

FIG. 5 is a perspective view of a filter bag housing as used in connection with present invention.

FIG. 6 is side view of the horizontal extraction vessel containing an array of filter bag housings as illustrated in FIG. 5.

DESCRIPTION OF THE INVENTION

The present invention as described herein is directed at systems and methods for extracting organic or botanical compounds from botanical materials. For purposes of this description, by "botanical materials" it is meant, but is not limited to, industrial hemp, *cannabis*, tobacco, hops, camelina, pennycress, soy beans, jatropha, distiller's dried grains solubles, plants and plant materials. Plants and plant materials are defined as any plant or plant part, including bark, wood, leaves, stems, roots, flowers, fruits, seeds, berries or parts thereof. The botanical or organic compounds to be extracted utilizing the present invention are generally materials to be used for a particular purpose with desirable medicinal properties, flavor, aroma, or nutritive quality that is removed from the tissue of the botanical materials, usually by treating the botanical materials with a solvent. An example of an organic botanical compound includes the family of cannabinoids, which those skilled in the art will recognize includes over 60 bi- and tri-cyclic compounds including, but not limited to, $\Delta^9$-tetrahydrocannabinol ("$\Delta^9$-THC"), $\Delta^8$-tetrahydrocannabinol ("$\Delta^8$-THC"), Cannabichromene ("CBC"), Cannabidiol ("CBD"), Cannabigerol ("CBG"), Cannabinol ("CBN") and the associated carboxylic acids of the cannabinoids listed above. Other botanical compounds include, but are not limited to, hop oil, bio-oil, nicotine, fragrances and essential oils. Essential oils include, but are not limited to, orange, menthe arvenis, peppermint, cedarweed, lemon, *eucalyptus globulis, litsea cubeba*, clove and spearmint.

Figure 1:
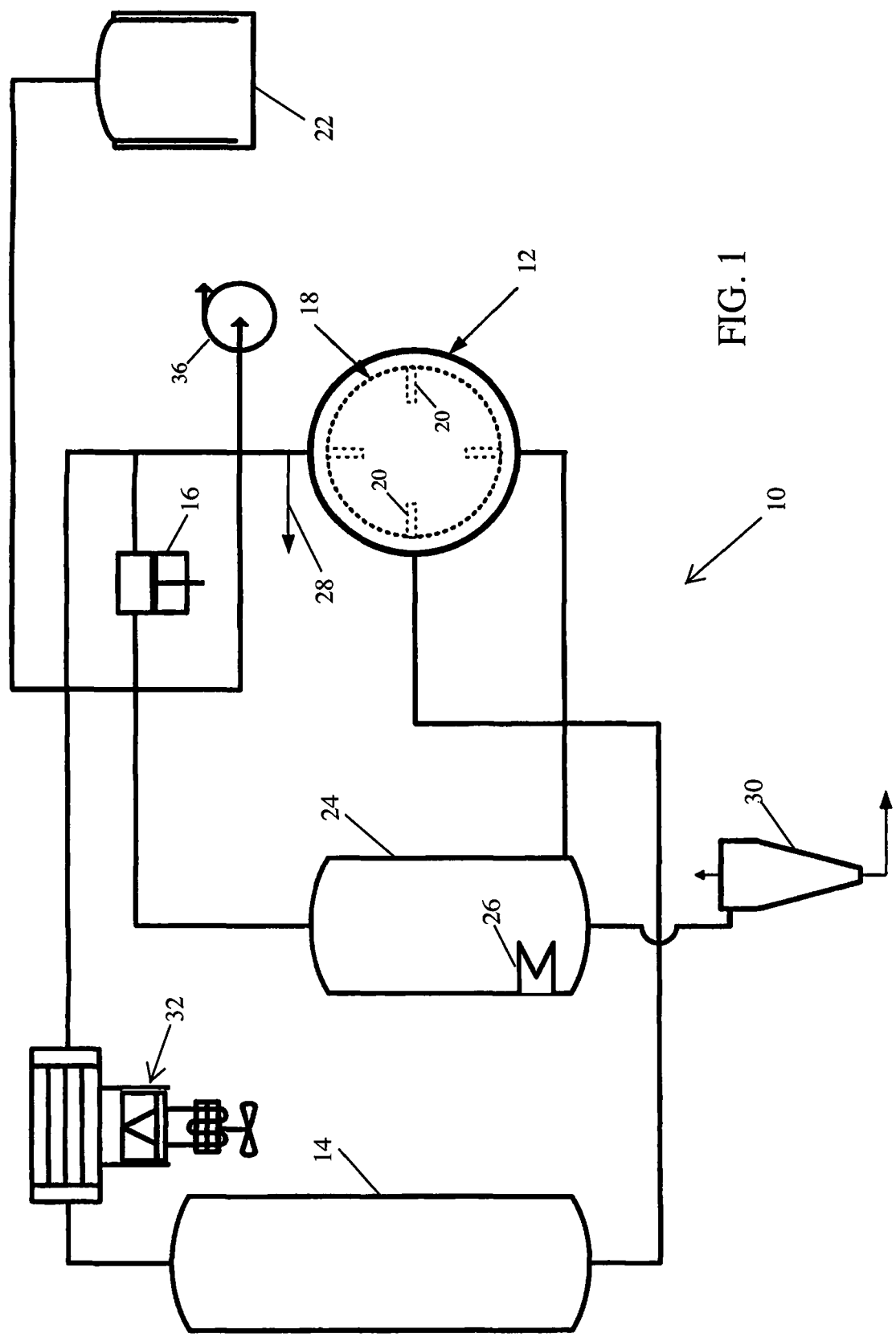
FIG. 1 is a diagram of the liquid carbon dioxide botanical extraction system utilizing a horizontal extraction chamber in accordance with the present invention.

Referring to FIG. 1, to obtain the botanical compound, a liquid carbon dioxide extraction system 10 is provided. The extraction system 10 is similar to the system taught and disclosed in commonly owned U.S. Pat. No. 6,851,148, the contents of which are incorporated herein by reference. The extraction system 10 includes an extraction vessel 12 for containing botanical materials, and a storage tank 14 containing a supply of liquid solvent, such as liquid carbon dioxide or liquid propane or combinations thereof. A compressor 16 pressurizes and transfers gas to the storage tank 14 to the extraction chamber 12. The compressor 16, which under the proper temperature and pressure, also transfers gas or dense phase gas from one vessel to another, moves densified gas from the storage vessel 14 to the extraction vessel 12, as well as moves densified gas and extractants from the extraction vessel 12.

Figure 2:
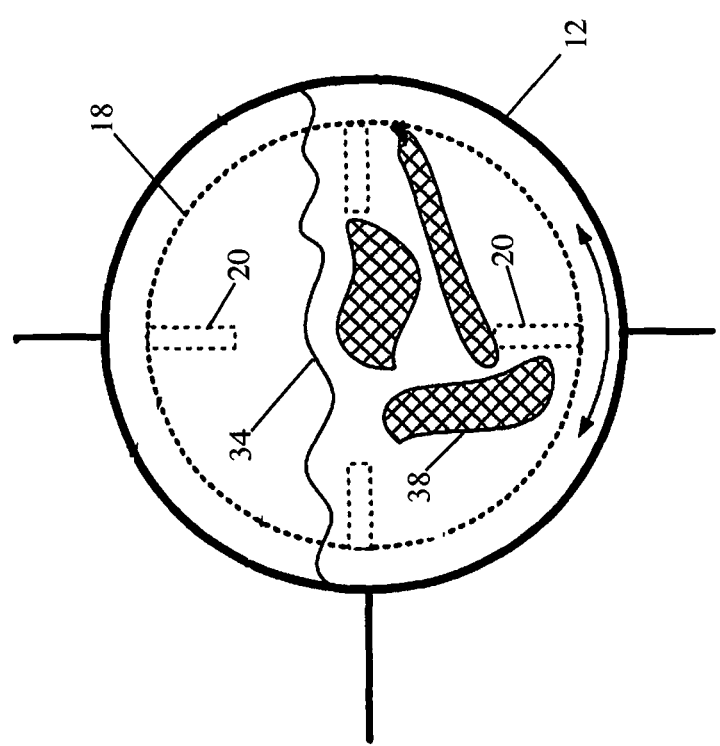
FIG. 2 is a cross-sectional view of the horizontal extraction chamber from FIG. 1.

As best illustrated in FIG. 2, the extraction chamber 12 includes a horizontally oriented basket 18 rotatably mounted therein for agitating botanical material during one or more extraction cycles. The basket 18 preferably includes one or more baffles 20 to assist in agitation. A transfer tank 22 contains an additional supply of liquid solvent and selectively communicates with the extraction vessel 12 so that additional solvent may be added to the system.

Returning to FIG. 1, the horizontal extraction vessel 12 is in fluid communication with a concentrator 24. The concentrator 24 is used to concentrate the organic compound obtained from the extraction vessel 12 by vaporizing carbon dioxide and removing the gaseous carbon dioxide from the concentrator 24. Vaporization in the concentrator 24 occurs at temperatures preferably below 25° C., including below 15° C. and even below 0° C. To vaporize the carbon dioxide to gaseous carbon dioxide, a heating fixture 26 is affixed to the concentrator 24. To optionally remove gaseous carbon dioxide, the concentrator 24 fluidly connects to the storage vessel 14, at lower pressure. In the instance where the storage vessel 14 is used, the pressure of the storage vessel 14 is lowered to a pressure that is below that of the concentrator 24.

The extraction system 10 further includes a separator 30 connected to the concentrator 24. The separator 30 is for separating the botanical materials from the concentrator 24 from the solvent. The separator 30 separates the organic compounds by boiling the solvent, such as carbon dioxide, to form a gas. The gas generated in the separator is expelled by pressure difference, leaving the organic compounds in the bottom of the separator. The separator 30 may optionally be connected to a heating unit (not shown) to maintain a desired temperature of the unit during depressurization. When the separator 30 is depressurized, an extract is removed. The extract consists of the organic compounds, water, and other extractants.

A refrigeration/condensation unit 32 is used to remove heat from gaseous solvents to condense and form liquid solvents, for example gaseous carbon dioxide to liquid carbon dioxide. The refrigeration/condenser unit 32 may also be used to lower the pressure of the saturated gaseous solvent. The concentrator heater 26 is used to deliver heat to the concentrator 24 whereby liquid solvent, for example liquid carbon dioxide, can be vaporized. A vacuum pump 36 is used to remove excess air in the extraction vessel 12 prior to commencing the extraction process.

During the extraction cycles, liquid solvent may be withdrawn from the extraction vessel 12, filtered and returned to the extraction vessel so that constant filtration is provided. Solvent gas may be withdrawn from the storage tank 14 so that the liquid therein boils. The resulting vapor may be raised in pressure and temperature by the compressor 16 and introduced into the liquid solvent in the extraction vessel 12 so that the liquid solvent is warmed and its extraction properties enhanced. A Pressure relief valve 28 may be optionally included to relieve pressure in the extraction vessel 12 in the event of an emergency system shutdown without venting gas to the atmosphere.

Preferably, the extraction system 10 in accordance with the present invention utilizes as a solvent dense carbon dioxide in its subcritical or liquid state. Extraction with subcritical liquid carbon dioxide ("SLCD") is preferably employed at a temperature of less than 25° C. while in the extraction vessel 12. However, it has been discovered that when extracting organic compounds, such as cannabinoids, from botanical materials, such as industrial hemp or *cannabis*, temperatures between −10° and 14° C. are more preferable. Further, and contrary to the teachings of the prior art, temperatures between −10° and 0° C. are most preferable. The preferred pressure range during extraction is between 400 and 724 psi (2.76 to 4.99 MPa). More preferably, the extraction is carried out at approximately 500 psi (3.45 MPa). It is believed that extraction of organic compounds from these botanical materials using SLCD under these conditions is favorable as the target organic compounds, such as cannabinoids and essential oils, are more soluble, whereas the unwanted compounds, such as sugars, polysaccharides, waxes and other undesirable products that may be contained in the plaint material, are not. The resulting extract, having a higher concentration of the target organic compounds (e.g., cannabinoids), requires less refinement to make ready for sale or further processing.

Alternatively, the extraction solvent can be liquid propane. When using liquid propane as the extraction solvent, a preferable temperature range is between 15° and 25° C., while a preferable pressure range is between 725 and 800 kPa. More preferably, the temperature is about 21° C. and the pressure about 758 kPa.

Figure 3:
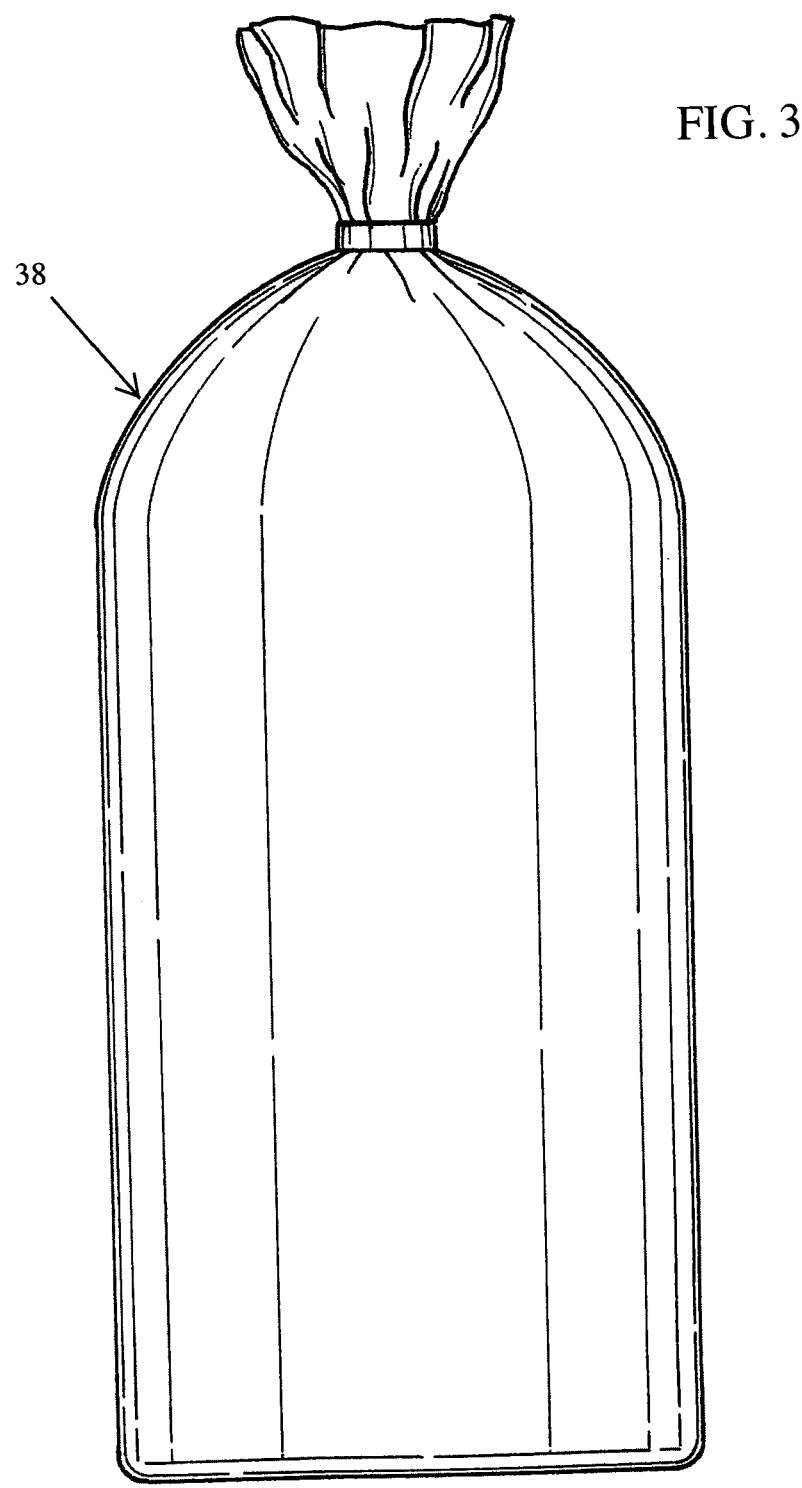
FIG. 3 is a perspective view of a filter bag as used in accordance with the present invention.

It has also been discovered that the quality of the organic compound extracted from the botanical material is greatly impacted through the use of filter bags 38, as illustrated in FIG. 3. By placing the botanical material within a filter bag 38, and then placing the filter bag 38 containing the botanical material into the extraction vessel 12, it has been surprisingly discovered that the extraction of the organic compounds is greatly enhanced. Without attempting to be bound by theory, it is believed that by containing the botanical materials within filter bags 38, the baffles 20 within the rotating basket impart greater impact onto the botanical material, thereby resulting in the SLCD having a more intimate contact and penetration of the botanical material to facilitate extraction of the organic compounds, all the while containing the botanical materials within a controlled volume. Preferably, the filter bags 38 are constructed of felt material having pores of 0.5 microns or larger. The filter bags 38 allow the SLCD, as well as the SLCD containing the organic compounds dissolved therein, to pass through while yet retaining the solids of the botanical material. Such filter bags 38 are commercially available from a variety of suppliers, including Filter Specialists, Inc., of Michigan City, Ind.

Figure 4:
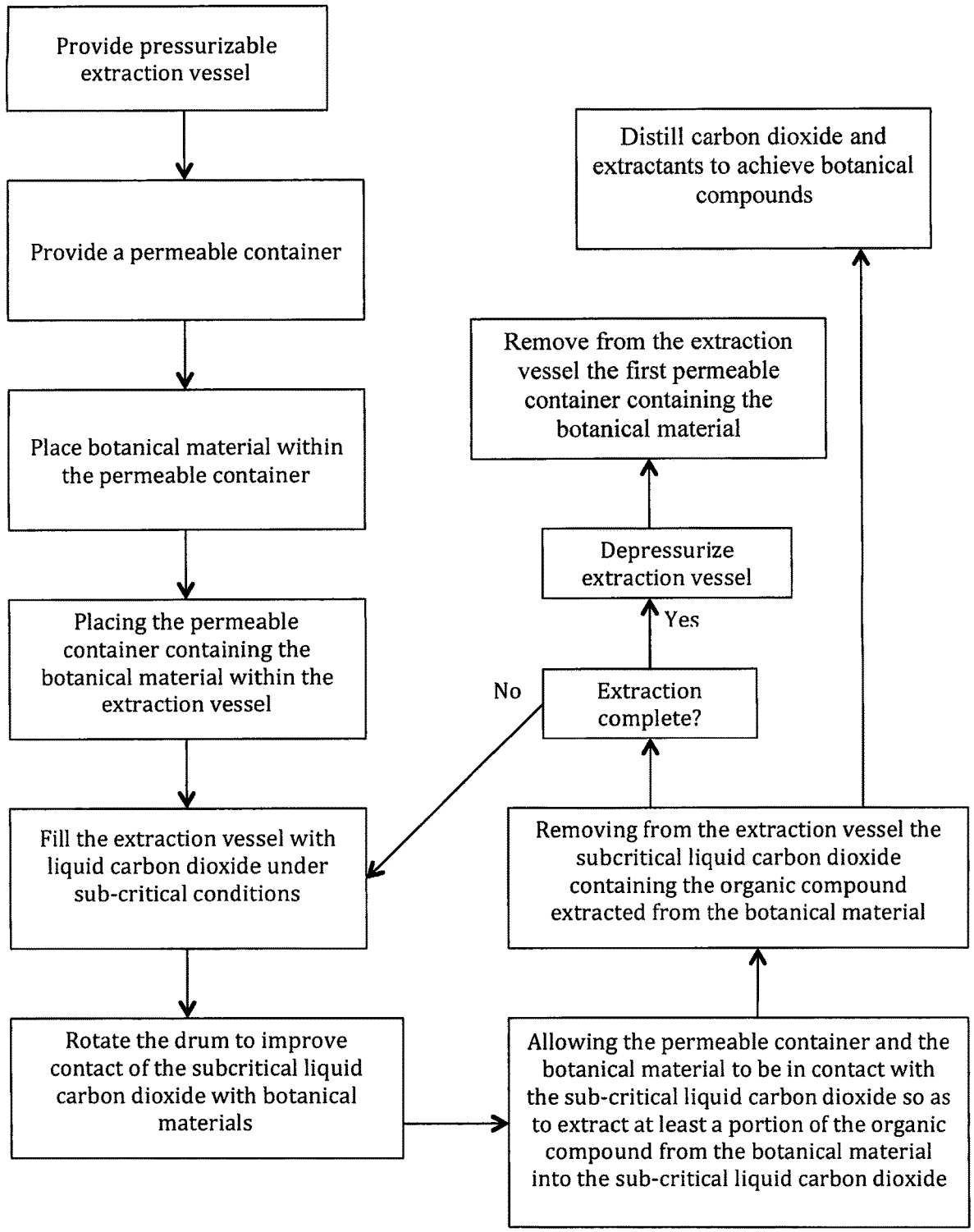
FIG. 4 is a flowchart of a first embodiment method of the present invention.

Referring now to the diagram of FIG. 4, in operation, the pressurizable extraction system 10 is provided, as well as the first permeable containers, or filter bags. The botanical materials to be treated are placed within the filter bags 38. The botanical materials themselves may be raw or dried, ground or whole, or previously processed, including having gone through a decarboxylation step. One or more filter bags 38 containing the botanical materials to be processed are then placed within the rotating basket 18 of the extraction vessel 12. The extraction vessel closure (not shown) is then secured. Excess air is removed from extraction vessel by the vacuum pump 36. Gaseous carbon dioxide is injected into the extraction vessel 12 via the concentrator 24, the storage tank 14 or the make-up carbon dioxide supply 22. Upon injecting the extraction vessel with the gaseous carbon dioxide, the final pressure is subcritical, optimally at the target extraction pressure of 500 psi (3.45 MPa). SCLD is then injected into the extraction vessel 12 from the storage tank 14 to a selected level 34 to, optimally, immerse the filter bags 38. Selective additives may optionally be added to the SCLD to modify the solubility of the extracting fluid. Preferably, the concentration of these additives is less than 5% by mass. Additives that may be used are those that are soluble in the SLCD at the operating conditions, including but not limited to ethanol, isopropanol, acetone, carbon dioxide soluble alcohols, carbon dioxide soluble ketones or carbon soluble substances, including terpenes, such as d-limonene, and glycol ethers, such as DPnB. The botanical materials are then exposed to the SLCD for a period of time until a sufficient quantity of extractables becomes solubilized in the SLCD, preferably between 10-15 minutes.

The extraction process is enhanced by rotating the basket 18 such that the baffles 20 come into contact with the filter bags 38. The basket 18 can be rotated in one direction at a rate between 1-200 RPM. Alternatively, the basket 18 can be rotated in one direction at a rate within the aforementioned range, then stopping for a period of time, then reversing direction at rate within the aforementioned range. Alternatively, or additionally, the extraction chamber 12 can be treated to a pressure spike whereby the pressure is rapidly decreased to a lower pressure, then increased back to the original pressure. Alternatively, the level of SLCD in the extraction chamber 12 may be set so as to cause the filter bags 38 to fall a distance off the paddles and into the liquid level, causing a splash, wherein extraction is enhanced.

Alternatively, as illustrated in FIGS. 5 and 6, the rotating drum 18 is fitted with a rack 40 for holding second permeable containers, filter bag baskets 42. Each filter bag basket 42, which is perforated, is capable of housing a filter bag 38 containing the botanical materials. The advantages of using the baskets 42 is to reduce the amount of agitation on the filter bags 38 and to evenly distribute the load in the extraction vessel. This allows the filter bags 38 to be rotated at high speeds without the risk of eccentric loading in the vessel. Such baskets are commercially available through SaniClean Strainers of Clifton, N.J.

Returning to FIG. 4, after between 10-15 minutes, or optionally up to 30 minutes, the SLCD now containing the extracted compounds is removed, and sent for further processing. The extraction chamber 12 may then be refilled with SLCD in the manner described, wherein the agitation process is repeated. The total number of baths is generally between 30-90 to achieve satisfactory removal of the organic compounds from the botanical materials.

Alternatively, a continuous bath mode may be employed. In the continuous bath mode, SLCD in injected into the extraction vessel to an optimal level and the agitation within the extraction vessel 12 is initiated. After a few minutes, for example between 3 to 5 minutes, a portion of the SLCD with organic compound extractants solubilized therein are removed from the extraction vessel 12 at a continuous rate to the concentrator 24. Concurrently, fresh SLCD is injected into the extraction vessel 12 such that the level of SLDC remains approximately the same. This process continues for up to 8 hours to fully remove the extractants. In this continuous bath operational mode, extraction of the organic compounds, for example cannabinoids, is continuous and occurs within a single bath. This continuous mode of operation provides advantages over multi-bath operation including less down time where the system is not extracting product, more efficient use of heat transfer equipment, and larger throughput of SLCD for shorter extraction periods.

Upon removal of the SLCD containing the extracted organic compounds from the extraction vessel 12, the solution is transferred to the concentrator 24. To make up for the SLCD removed from the extraction vessel 12, SLCD from the storage tank 14 is injected into the extraction vessel 12 to replicate the extraction conditions. Gaseous carbon dioxide in the concentrator 24 is then removed by applying heat via heater 26, lowering the pressure in the storage tank 14, removing gas from the gas head of the concentrator 24 by the compressor 16, or by a combination thereof. This process is stopped when the optimal level of liquid carbon dioxide and extract is obtained in the concentrator 24.

The SLCD containing the extractants collected in the bottom of the concentrator 24 is then conveyed to the separator 30. Separation of extractants from liquid carbon dioxide is accomplished by removing gaseous carbon dioxide from the separator 30, or by heating the SLCD in the concentrator 24 to convert the SLCD to its gaseous phase, or by combinations of both. As the extractants are now not soluble in gaseous carbon dioxide, the extractants fall out of solution and collect in an extract receiver inside the separator 30. Alternatively, as low temperature extractions can yield valuable products, solid carbon dioxide and extractants may be collected and removed from the separator 30, which can be further separated in a subsequent separation step outside the extraction system 10. The aforementioned process steps are repeated until the extraction sequence is completed.

After all SLCD is removed from the extraction vessel 12, gaseous carbon dioxide is removed from the extraction chamber 12 by the compressor 16 until the final recovery pressure value is achieved. Gaseous carbon dioxide remaining in the extraction chamber 12 is vented out of the extraction vessel. The extraction vessel closure is then opened and the filter bags 38 containing the now extracted botanical materials are removed from the extraction vessel 12 wherein the extraction run is completed.

Figure 7:
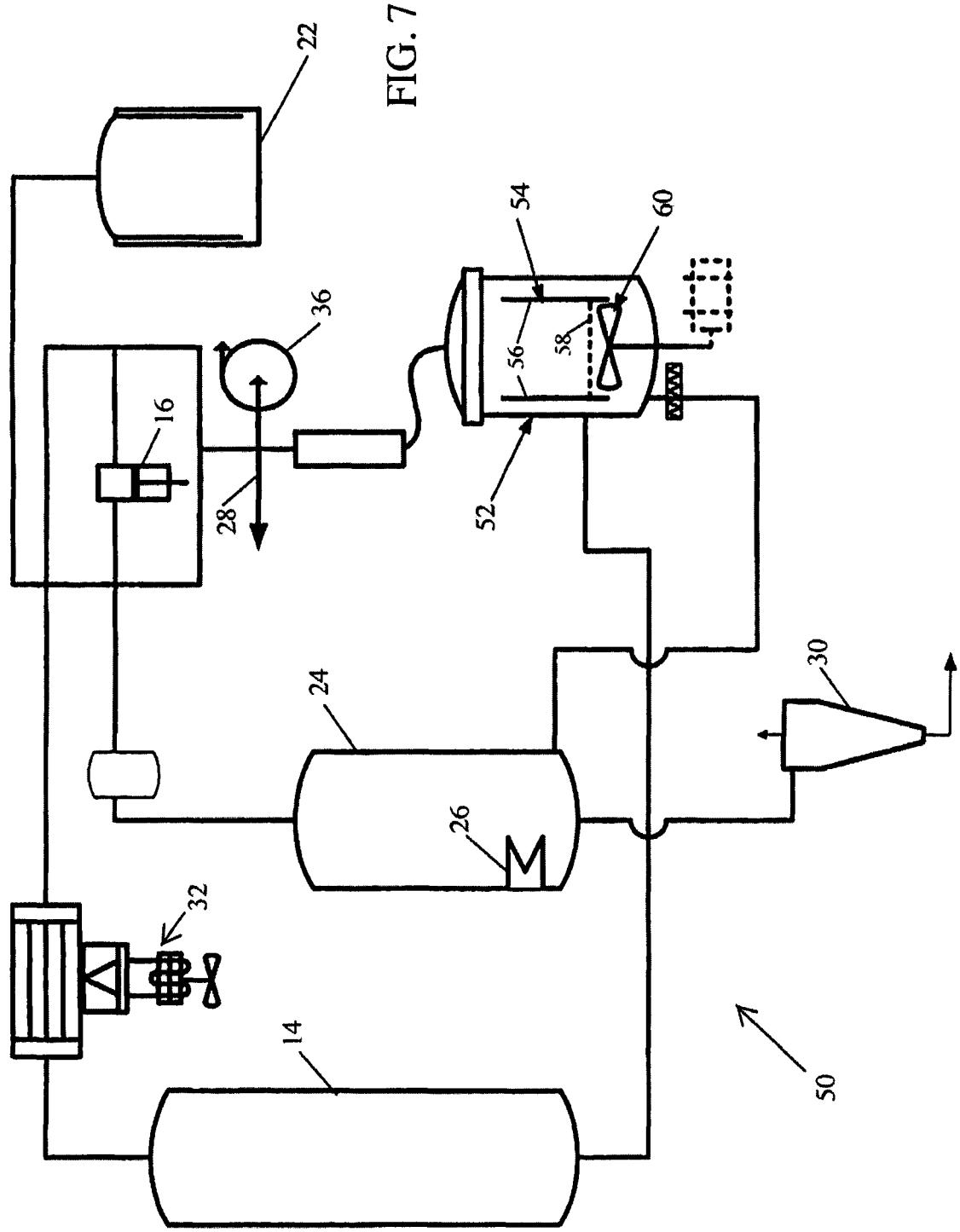
FIG. 7 is a diagram of a liquid carbon dioxide botanical extraction system utilizing a vertical extraction vessel in accordance with the present invention.
Figure 8:
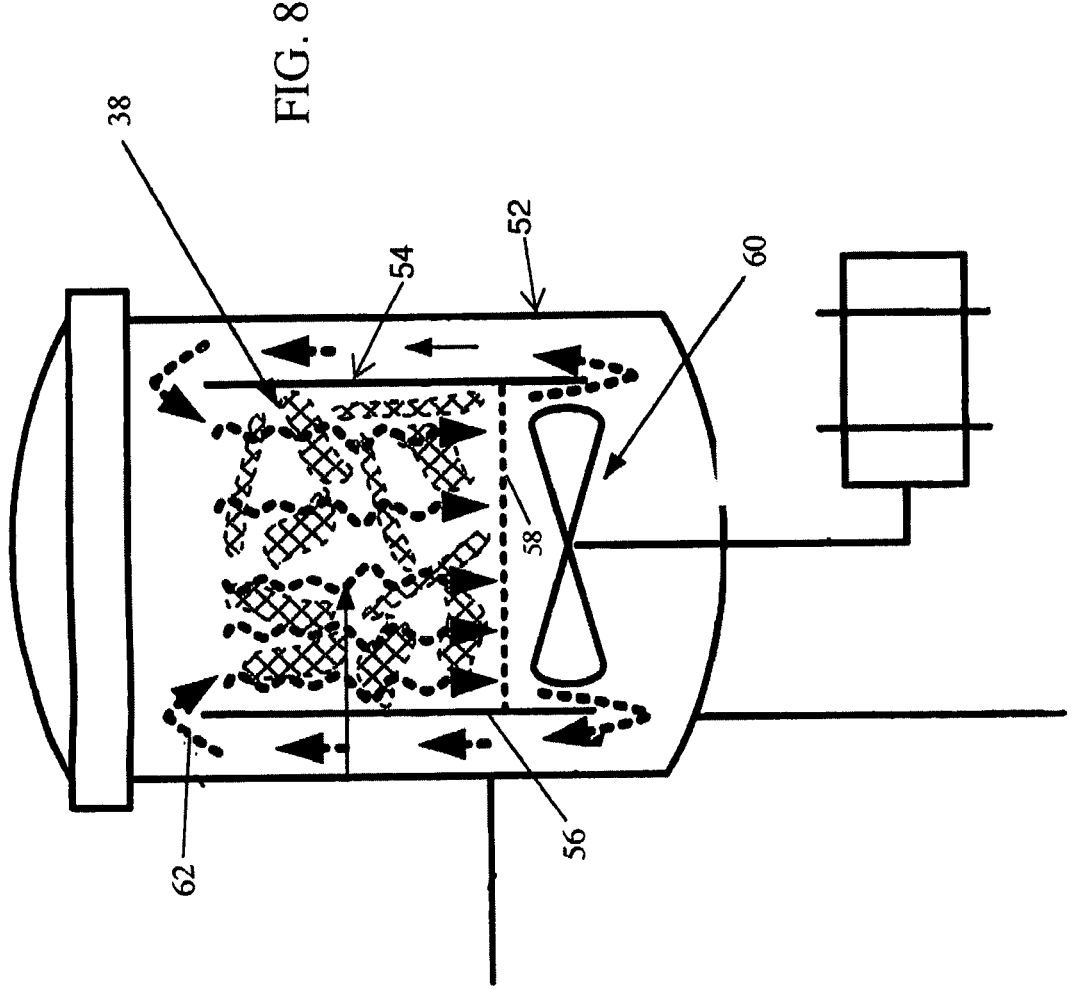
FIG. 8 is an enlarged detail view of the liquid carbon dioxide flow through botanical materials in accordance with the extraction system of FIG. 7.

Referring now to FIG. 7, a diagram of a second alternative extraction system 50 is illustrated. The alternative embodiment 50 contains many of the salient features of the first embodiment 10, wherein like references correspond to similar parts as previously described. However, instead of horizontally aligned rotating basket, the alternative embodiment 50 utilizes an extraction vessel equipped with an interior basket 54 that is vertically mounted and fixed to the inside of the chamber. SLCD is again used in temperature and pressure ranges as previously described. As illustrated in FIG. 8, the interior basket 54 has solid vertical sidewalls 56 and a perforated floor 58 which separates the filter bags 38 containing the botanical material from an impeller 60. The impeller 60 draws liquid through an inner portion of the basket 54 containing the filter bags 38 filled with botanical materials, and circulates the SLCD around the exterior of the basket 54 in the direction of arrows 62. The direction and speed of impeller rotation can be modified to optimize the extraction efficiency.

Figure 9:
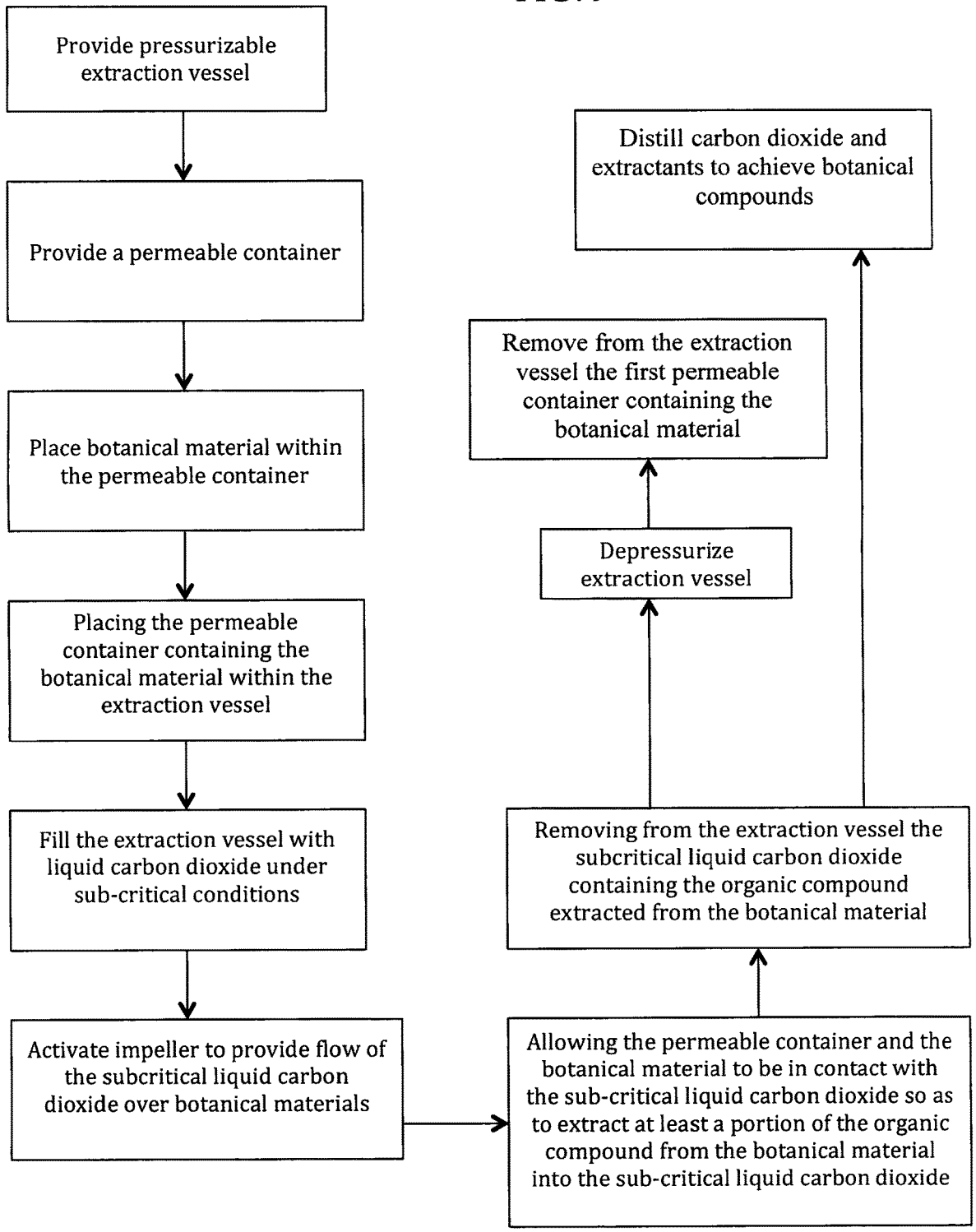
FIGS. 9 and 10 are flowcharts of alternative embodiment methods of the present invention.
Figure 10:
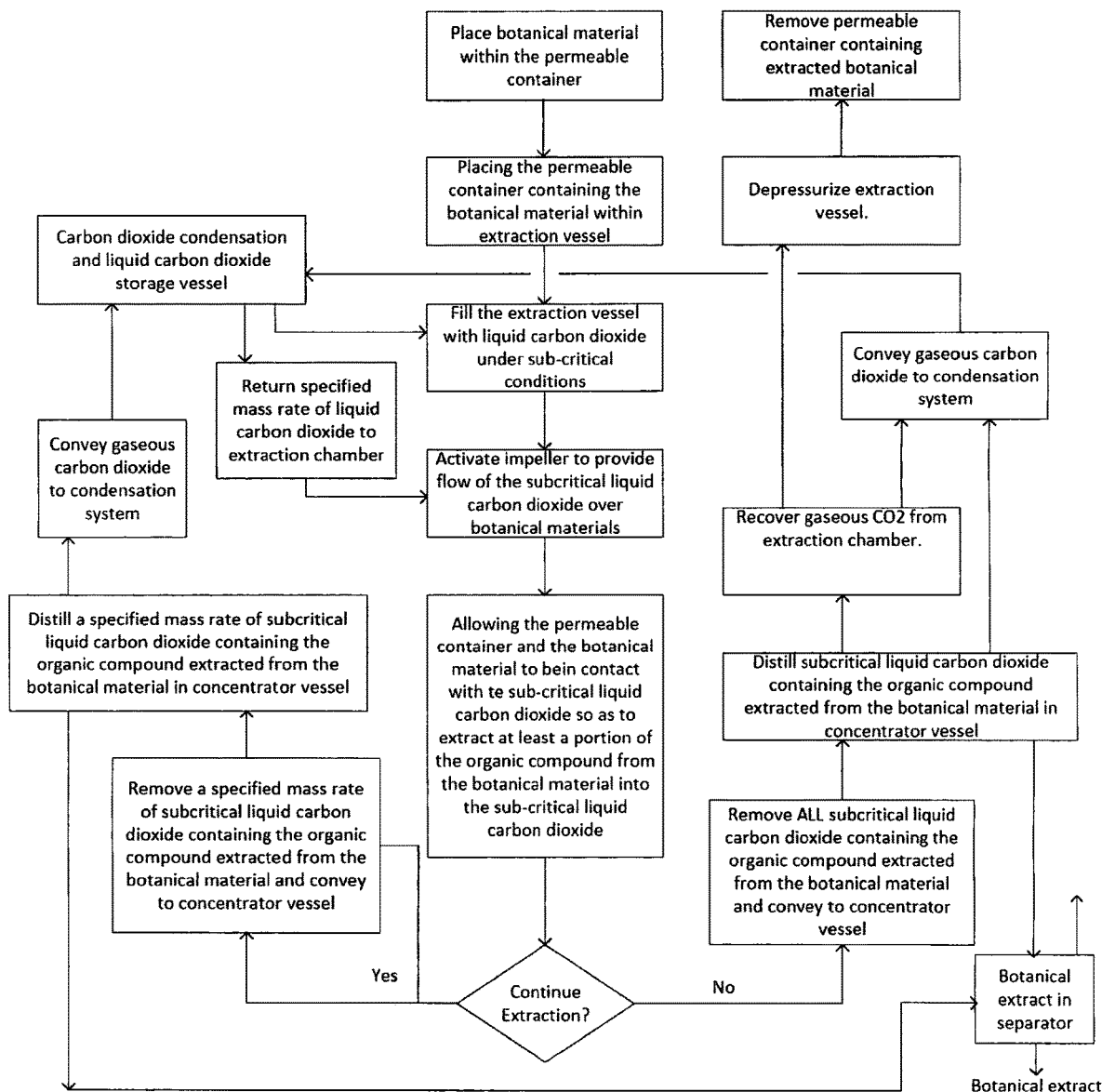

Referring now to the diagram of FIGS. 9 and 10, in operation, the pressurizable extraction system 50 is provided, as well as the first permeable containers, or filter bags 38. The botanical materials to be treated are placed within the filter bags 38. The botanical materials themselves may be raw or dried, ground or whole, or previously processed, including having gone through a decarboxylation step. One or more filter bags 38 containing the botanical materials to be processed are then placed within the fixed vertical basket 54 of the extraction vessel 50. The extraction vessel closure (not shown) is then secured. Excess air is removed from extraction vessel by the vacuum pump 36. Gaseous carbon dioxide is injected into the extraction vessel 52 via the concentrator 24, the storage tank 14 or the make-up carbon dioxide supply 22. Upon injecting the extraction vessel with the gaseous carbon dioxide, the final pressure is subcritical, optimally at the target extraction pressure of 500 psi (3.45 MPa). SCLD is then injected into the extraction vessel 52 from the storage tank 14 to, optimally, immerse the filter bags 38. Selective additives may optionally be added to the SCLD to modify the solubility of the extracting fluid. Preferably, the concentration of these additives is less than 5% by mass. Additives that may be used are those that are soluble in the SLCD at the operating conditions, including but not limited to ethanol, isopropanol, acetone, carbon dioxide soluble alcohols, carbon dioxide soluble ketones or carbon soluble substances, including terpenes, such as d-limonene, and glycol ethers, such as DPnB. The botanical materials are then exposed to the SLCD for a period of time until a sufficient quantity of extractables becomes solubilized in the SLCD, preferably between 10-15 minutes.

The extraction process is enhanced by activating the impeller 60 to induce a flow of solvent through the filter bags 38 as previously described. After the extraction is complete, typically between 10-15 minutes, but can be up to 30 minutes, the SLCD now containing the extracted compounds is removed, and sent for further processing.

Alternatively, a continuous bath mode may be employed. In the continuous bath mode, SLCD in injected into the extraction vessel to an optimal level and the agitation within the extraction vessel 52 is initiated. After about 3 to 5 minutes, a portion of the SLCD with organic compound extractants solubilized therein are removed from the extraction vessel 52 at a continuous rate to the concentrator 24. Concurrently, fresh SLCD is injected into the extraction vessel 52 such that the level of SLDC remains approximately the same. In this continuous bath operational mode, extraction of the organic compounds, for example cannaboids, is continuous and occurs within a single bath. This continuous mode of operation provides advantages over multi-bath operation including less down time where the system is not extracting product, more efficient use of heat transfer equipment, and larger throughput of SLCD for shorter extraction periods.

Upon removal of the SLCD containing the extracted organic compounds from the extraction vessel 52, the solution is transferred to the concentrator 24. To make up for the SLCD removed from the extraction vessel 52, SLCD from the storage tank 14 is injected into the extraction vessel 52 to replicate the extraction conditions. Gaseous carbon dioxide in the concentrator 24 is then removed by applying heat via heater 26, lowering the pressure in the storage tank 14, removing gas from the gas head of the concentrator 24 by the compressor 16, or by a combination thereof lowering the pressure in the storage tank and removing gas from the gas head of the concentrator vessel by the compressor. This process is stopped when the optimal level of liquid carbon dioxide and extract is obtained in the concentrator 24.

The SLCD containing the extractants collected in the bottom of the concentrator 24 is then conveyed to the separator 30. Separation of extractants from liquid carbon dioxide is accomplished by lowering the pressure of the separation vessel by removing gaseous carbon dioxide from the separator 30, or by heating the SLCD in the concentrator 24 to convert the SLCD to its gaseous phase, or by combinations of both. As the extractants are now not soluble in gaseous carbon dioxide, the extractants fall out of solution and collect in an extract receiver inside the separator 30. Heat may be optimally added to sublime the solid CO2 to maintain the desired extraction temperature. Alternatively, as low temperature extractions can yield valuable products, solid carbon dioxide and extractants may be collected and removed from the separator 30, which can be further separated in a subsequent separation step outside the extraction system 50. The aforementioned process steps are repeated until the extraction sequence is completed.

After all SLCD is removed from the extraction vessel 52, gaseous carbon dioxide is removed from the extraction chamber 52 by the compressor 16 until the final recovery pressure value is achieved. Gaseous carbon dioxide remaining in the extraction chamber 52 is vented out of the extraction vessel. The extraction vessel closure is then opened and the filter bags 38 containing the now extracted botanical materials are removed from the extraction vessel 52 wherein the extraction run is completed.

Although the present invention has been described with reference to preferred embodiments, workers skilled in the art will recognize that changes may be made in form and detail without departing from the spirit and scope of the invention.

The invention claimed is:

1. A process for extracting cannabinoids from hemp or *cannabis* consisting essentially of:
    providing a pressurizable extraction vessel having a rotatable drum;
    providing a solvent permeable container;
    placing the hemp or *cannabis* within the solvent permeable container;
    placing the solvent permeable container within the pressurizable extraction vessel;
    filling the pressurizable extraction vessel with subcritical liquid carbon dioxide;
    allowing the hemp or *cannabis* to be in contact with the subcritical liquid carbon dioxide under subcritical conditions so as to extract at least a portion of the cannabinoids from the hemp or *cannabis* into the subcritical liquid carbon dioxide;
    removing from the pressurizable extraction vessel, the subcritical liquid carbon dioxide containing the cannabinoids extracted from the hemp or *cannabis*; and
    separating the subcritical carbon dioxide solvent from the cannabinoids to yield extracted cannabinoids.

2. The process of claim 1, wherein the rotatable drum consists essentially of baffles.

3. The process of claim 2, consisting essentially of rotating the drum in order for the baffles to contact a permeable container.

4. The process of claim 1, wherein the subcritical conditions are at a pressure between 2.76 MPa to 4.99 MPa and at a temperature between 10° C. to 14° C.

5. The process of claim 1, wherein the solvent permeable container is constructed from a porous material having pores of at least 0.5 microns in diameter.

6. The process of claim 1, wherein the permeable container is a filter bag.

* * * * *